United States Patent [19]

Tullis

[11] Patent Number: 5,919,619
[45] Date of Patent: Jul. 6, 1999

[54] OLIGONUCLEOTIDE THERAPEUTIC AGENT AND METHODS OF MAKING SAME

[75] Inventor: Richard H. Tullis, La Jolla, Calif.

[73] Assignee: Molecular Biosystems, Inc., San Diego, Calif.

[21] Appl. No.: 08/455,760

[22] Filed: May 31, 1995

Related U.S. Application Data

[63] Continuation of application No. 08/078,768, Jun. 16, 1993, which is a continuation of application No. 07/633,452, Dec. 20, 1990, abandoned, which is a continuation of application No. 07/355,140, May 15, 1989, Pat. No. 5,023,243, which is a continuation of application No. 07/140,916, Dec. 29, 1987, abandoned, which is a continuation of application No. 07/002,014, Jan. 9, 1987, abandoned, which is a continuation of application No. 06/314,214, Oct. 23, 1981, abandoned.

[51] Int. Cl.[6] ................................................. A61K 48/00
[52] U.S. Cl. .......................... 435/6; 435/317.1; 435/91.1; 435/325; 514/44
[58] Field of Search .......................... 435/6, 91.1, 172.1, 435/172.3, 320.1, 69.1–70.1, 71.1–71.3, 252.3–252.35, 325, 317.1; 436/63, 94, 504; 514/44; 935/34, 77, 78; 536/24.3–25.3

[56] References Cited

U.S. PATENT DOCUMENTS

| | | |
|---|---|---|
| 4,399,216 | 8/1983 | Axel et al. . |
| 4,469,863 | 9/1984 | Ts'o et al. . |
| 5,023,243 | 6/1991 | Tullis . |

OTHER PUBLICATIONS

Miller, Paul S., et al., "Effects of a Trinucleotide Ethyl Phosphotriester, G"'p (Et)G"'p (Et)U, on Mammalian Cells in Culture," *Biochemistry* vol. 16, No. 9, 1988–1996 (1977).
Miller, Paul S., et al., "Biochemical and Biological Effects of Nonionic Nulceic Acid Methylphosphonates," *Biochemistry* vol. 20, No. 7, 1874–1880 (1981).
Jayaraman, Krishna, et al., "Selective inhibition of *Escherichia coli* protein synthesis and growth by nonionic oligonucleotides complementary to the 3' end of 16S rRNA," *Proc. Natl. Acad. Sci, USA* vol. 78, No. 3, 1537–1541 (1981).
Paterson, Bruce M., et al., "Structural gene identification and mapping by DNA–mRNA hybrid–arrested cell–free translation," *Proc. Natl. Acad. Sci, USA* vol. 74, No. 10, 4370–4374, (1977).
Hastie, Nicholas D., et al., "Analysis of mRNA populations by cDNA–mRNA hybrid–mediated inhibition of cell–free protein synthesis," *Proc. Natl. Acad. Sci, USA* vol. 75, No. 3, 1217–1221, (1978).
Wallace, R. Bruce, et al., "Hybridization of synthetic oligodeoxyribonucleotides to Φx174 DNA: the effect of single base pair mismatch," *Nucleic Acids Research* vol. 6, No. 11, 3543–3557, (1979).
Zamecnik, Paul C., et al., "Inhibition of Rous sarcoma virus replication and cell transformation by a specific oligodeoxynucleotide," *Proc. Natl. Acad. Sci. USA*, vol. 75, No. 1, 280–284, (1978).
Stephenson, Mary L., et al., "Inhibition of Rous sarcoma viral RNA translation by a specific oligodeoxyribonucleotide," *Proc. Natl. Acad Sci. USA*, vol. 75, No. 1, 285–288, (1978).
Miller, Paul S., "Synthesis of Oligodeoxyribonucleotide Ethyl Phosphotriesters and Their Specific Complex Formation with Transfer Ribonucleic Acid," *Biochemistry*, vol. 13, No. 24, 4887–4896, (1974).
Barrett, J.C., "Inhibitory Effect of Complex Formation with Oligodeosyribonucleotide Ethyl Phosphotriesters on Transfer Ribonucleic Acid Aminoacylation," *Biochemistry*, vol. 13, No. 24, 4897–4906, (1974).
E. De Clerq, et al., "Interferon Induction Increased through Chemical Modification of a Synthetic Polyribonucleotide," pp. 1137–1139 (1969).
Szostak, J.W., et al., "Hybridization with Synthetic Oligonucleotides," *Methods in Enzymology*, vol. 68, 419–428, (1979).
Goodchild, John, "Conjugates of Oligonucleotides and Modified Oligonucleotides: A Review of Their synthesis and Properties," vol. 1, No. 3, 165–187, (1990).
Uhlmann, Eugen, et al., "Antisense Oligonucleotides: A New Therapeutic Principle," *Chemical Reviews*, vol. 90, No. 4, 543–562, (1990).
Tullis, Richard, et al., "Antisense Applications of Synthetic Nucleic Acids," *Biotechnology International* pp. 79–88 (1991).
*The Riboncleic Acids*, 2nd ed., edited by P.R. Stewart and D.L. Letham, pp. 81–128; 233–237; 239–269 (1977) Springer–Verlag, N.Y.
*Biochemistry*, 2nd ed., Lehninger, A.L. "The Molecular Basis of Cell Structure and Function," pp 398–399 (1970) Worth Publishers, Inc.
*Cold Spring Harbor Symposia on Quantitative Biology*, vol. XLII, "Chromatin", Salser, W. "Globin mRNA Sequences: Analysis of Base Pairing and Evolutionay Implications," pp. 985–1002 (1978).
Haeuptle, Marie–Therese, et al., "Translation arrest by oligodeoxynucleotides complementary to mRNA coding sequences yields polypeptides of predetermined length," *Nucleic Acids Research* vol. 14, No. 3, 1427–1448, (1986).

(List continued on next page.)

*Primary Examiner*—James Martinell
*Attorney, Agent, or Firm*—Townsend and Townsend and Crew LLP

[57] ABSTRACT

For use in controlling biologic functions in an organism, a stabilized oligonucleotide, preferably in a phosphotriester form, having a base sequence substantially complementary to a portion of messenger ribonucleic acid coding for a bological component, such as a protein, of the organism. The oligonucleotide has about fourteen bases or more, such as twenty-three bases, and can be a deoxyribonucleotide. The oligonucleotide sequence can be derived from the organism's ribonucleic or deoxyribonucleic acid that codes for a vital protein, and can be synthesized in bulk either chemically or by insertion into a plasmid.

13 Claims, 5 Drawing Sheets

OTHER PUBLICATIONS

Britten, R.J., et al., "Analysis of Repeating DNA Sequences by Reassociation," *Methods in Enzymology* vol. 29, 363–418, (1974).

Shen, T.Y., "Nucleosides and Nucleotides as Potential Therapeutic Agents," *Angrew. Chem. Internat.* vol. 9, 678–689, (1970).

Blake, Kathleen R., et al., "Inhibition of Rabbit Globin mRNA Translation by Sequence–Specific Oligodeoxyribonucleotides," *Biochemistry* vol. 24, No. 22, 6132–6138 (1985).

Heindell, Howard C., et al., "The Primary Sequence of Rabbit α–Globin mRNA," *Cell* vol. 15, 43–54, (1978).

Efstratiadia, Argirls, et al., "The Primary Structure of Rabbit β–Globin mRNA as Determined from Cloned DNA," *Cell* vol. 10, 571–585, (1977).

Gallo, Kathleen A., et al., "Alkyl phosphotriester modified oligodeoxyribonucleotides. V. Synthesis and absolute configuration of $R_p$ and $S_p$ diastereomers of an ethyl phosphotriester (E1) modified EcoR1 recognition sequence d[GGAA(E1)TTCC]. A synthetic approach to regio–and stereospecific ethylation–interference studies," *Nucleic Acids Research* vol. 14, No. 18, (1986).

Befort, N., et al., "Inhibition of Viral Multiplication by Homologous Methylated Ribonucleic Acids", *Chem. Biol. Interactions* vol. 9, 181–185, (1984).

Summerton, James, "Intracellular Inactivation of Specific Nucleotide Sequences: A General Approach to the Treatment of Viral Diseases and Virally–mediated Cancers," *J. theor. Biol.* vol. 78, 77–99, (1979).

*Comprehensive Biochemistry*, vol. 19B, Part I, edited by Maarcel Florkin, pp. 1–76 (1980). Elsevier Scientific Publishing Company, N.Y.

Mevarech, Moshe, et al., "Detection of Gastrin–specific mRNA Using Olihodeoxynucleotide Probes of Defined Sequence," *The Journal of Biological Chemistry* vol. 254, No. 16, 7472–7475, (1979).

Gubler, Ueli, et al., "Detection and partial characterization of proenkephalin mRNA," *Proc. Natl. Acad. Sci. USA* vol. 78, No. 9, 5484–5487, (1981).

Agarwal, Ken L., et al., "A General Method for Detection and Characterization of an mRNA using an Oligonucleotide Probe," *J. Biol. Chem* vol. 256, 1023–1028 (1981).

Summerton, James, et al., "Sequence–specific Crosslinking Agents for Nucleic Acids. Use of 6–Bromo–5,5–dimethoxyhexanohydrazide for Crosslinking Cytidine to Guanosine and Crosslinking RNA to Complementary Sequences of DNA", *J. Mol. Biol.* vol. 122, 145–162, (1978).

Blake, Kathleen R., et al., *Biochemistry*, vol. 24, 6139–6145 (1985).

Pless, Reynaldo C., et al., "Duplex Formation of a Nonionic Oligo(deoxythymidylte) Analogue [Heptadeoxythymidylyl–(3'–5")–deoxythymidine Heptaethyl Ester (d[Tp(Et)]–T)]with Poly (deoxyadenylate). Evaluation of the Electrostatic Interaction," *Biochemistry*, vol. 16, No. 6, 1239–1250 (1977).

Griveva, N.I., et al., "Alkylating Derivatives of Nucleic Acid Components . . . ," *Translated from Izvestiya*, Sibirskogo Otdelemdya Akadem: Nauk SSSR Seriaya Kolmicheskikh Nauk vol. 5, 118–124 (1968).

Karpova, G. G., et al., "Selective Alkylation of Poly (A) Tracts of RNA Inside the Cell with the Derivative of Ethyl Ester of Oligothymidilate Bearing –2–Chloroethylmamino Group," *FEBS Letters* vol. 122, No. 1, 21–24, (1980).

Liebhaber, Stephen A., et al., "Inhibition of mRNA Translation by Antisense Sequences," *Gene Regulation: Biology of Antisense RNA and DNA* (1992). pp. 163–174.

Pluskal, M.G., et al., "Isolation of an Oligonucleotide, a Potent Inhibitor of Eukaryotic and Viral Messenger Ribonucleic Acid Translaion, from Chick Embryonic Muscle," *Biochem. Soc. Trans.*, vol. 7, No. 5, 1091–1093 (1979).

Stebbing, N., "The Design of Antiviral Agents," *Pharm. Ther.*, vol. 6, 291–321,324, and 325 (1979).

Itakura, K., et al., "Chemical DNA Synthesis and Recombinant DNA Studies," *Science*, vol. 209, 1401–1405 (1980).

Koeffler, H.P., et al., "Regional assignment of genes for human α–globin and phosphoglycollate phosphatase to the short arm of chromosome 16," *Proc. Natl. Acad. Sci, USA*, vol. 78, No. 11 7015–7018 (1981).

Shulman, et al., "A better cell line for making hybridomas secreting specific antibodies," *Nature*, vol. 276, 269–270 (1978).

Steglich, C., et al., "Mutations Causing Deficiency of APRT in Fibroblasts Cultured from Human Heterozygous for Mutant APRT Alleles," *Somatic Cell Genetics*, vol. 8, No. 1, 115–141 (1982).

*Monoclonal Hybridoma Antibodies: Techniques and Applications*, Edited by Hurrell, J.G.R., Ph.D., pp. 16–17, (1982) CRC Press, Inc.

Blann, D.,"Cell hybrids: an important new source of antibody production," *Journal Laboratory Sciences*, vol. 36, 329–338 (1979).

Tennant, R.W., et al., "Effects of Poly(2'–O–Methyladenylic Acid) on Susceptibility and Antogenous Immunity to RNA Tumor Virus Oncogenesis In Vivo," *Proc. Nat. Acad. Sci. USA*, vol. 71, No. 8, 3167–3171 (1974).

Arya, S.K., et al., "Inhibition of RNA Directed DNA Polymerase of Murine Leukemia Virus by 2'–0–Alkylaed Polyadenylic Acids," *Biochemical and Biophysical Research Communications*, vol. 59, No. 2. 608–615 (1974).

*Modern Genetics*, 2nd Edition, Ayala, F.J. et al., "Renaturation Kinetics of DNA," pp. 263–267, 1984 The Benjamin/Cummings Publishing Company, Inc.

Miyoshi, K., et al., "Solid Phase Synthesis of Nonadecathymidylic Acid by the Phosphotriester Approach," *Tetrahedron Letters*, No. 38, 3635–3638 (1979).

*Analogues of Viral Genomes*, Pitha, P.M., pp. 349–359.

Gura, Science 270: 575 (1995).

Rojanasakul: Adv. Drug Delivery Rev. 18: 115 (1996).

Cook, in Antisense Research and Applications, 1993, Crooke et al (ed.), CRC Press, Inc., Boca Raton, Fla, pp. 149–187.

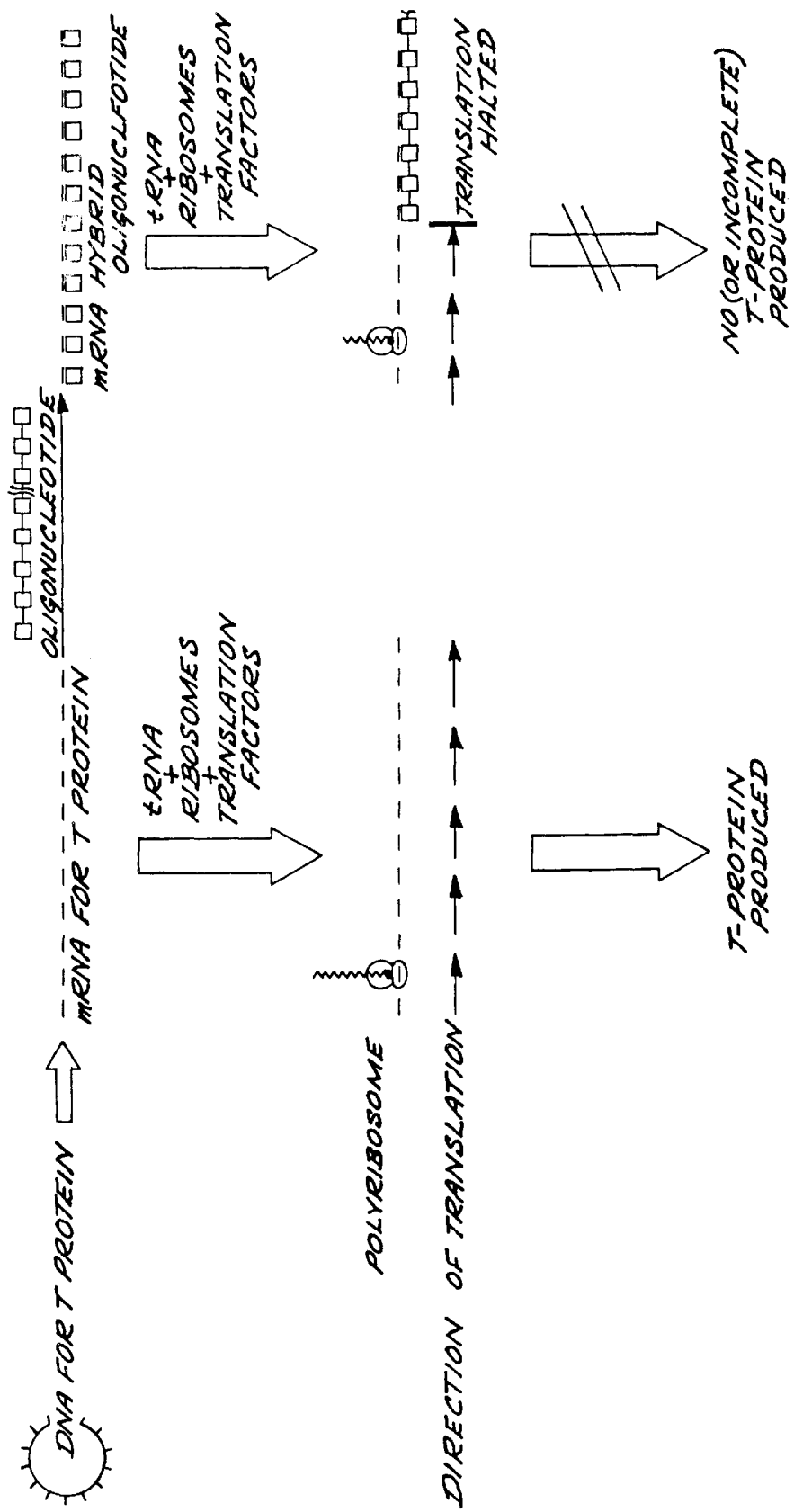

FIG. 3

OLIGONUCLEOTIDE SPECIFIC FOR SV-40 T PROTEIN

VIRAL DNA (CODING)   3'...G A A A C G T T T C T A C C T A T T T C...5'

VIRAL T PROTEIN
mRNA   5'...C U U U G C A A A G A U G G A U A A A G...3'

T PROTEIN SPECIFIC
OLIGONUCLEOTIDE   3'...G A A A C G T T T C T A C C T A T T T C...5'

FIG. 7

OLIGONUCLEOTIDE SPECIFIC FOR FOLLICLE STIMULATING HORMONE

PROTEIN SEQUENCE:
  N TERMINUS....THR TRP CYS ALA GLY TYR CYS TYR THR...C TERMINUS mRNA PREDICTED:
  5' END   ACX UGG UGC GCX GGX UAC UGU UAC ACX   3' END

FSH OLIGONUCLEOTIDE FAMILY:
  3' END   TCG ACC ACC CGG CCG ATG ACG ATG TG-   5' END
           (T)         (T) (T)

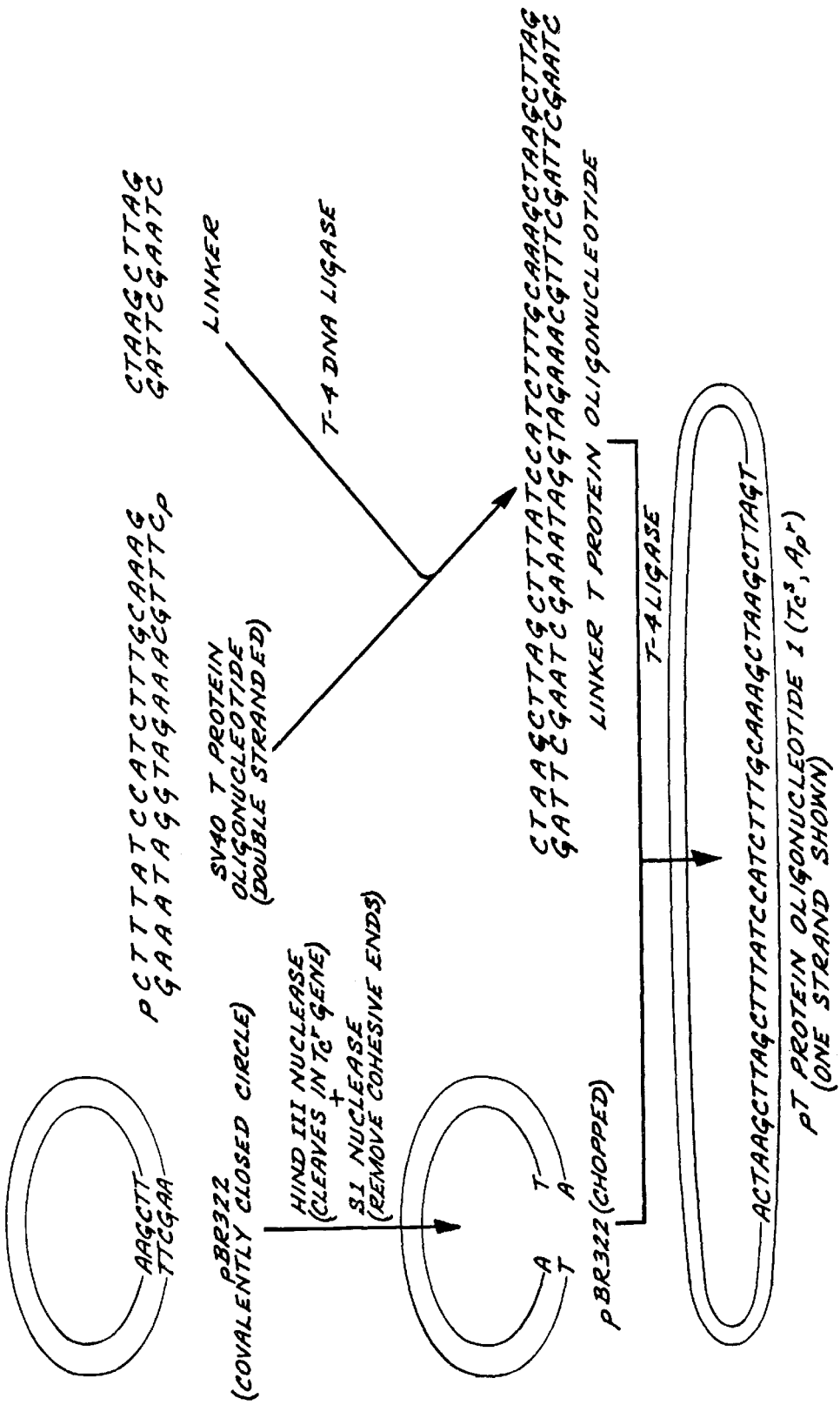

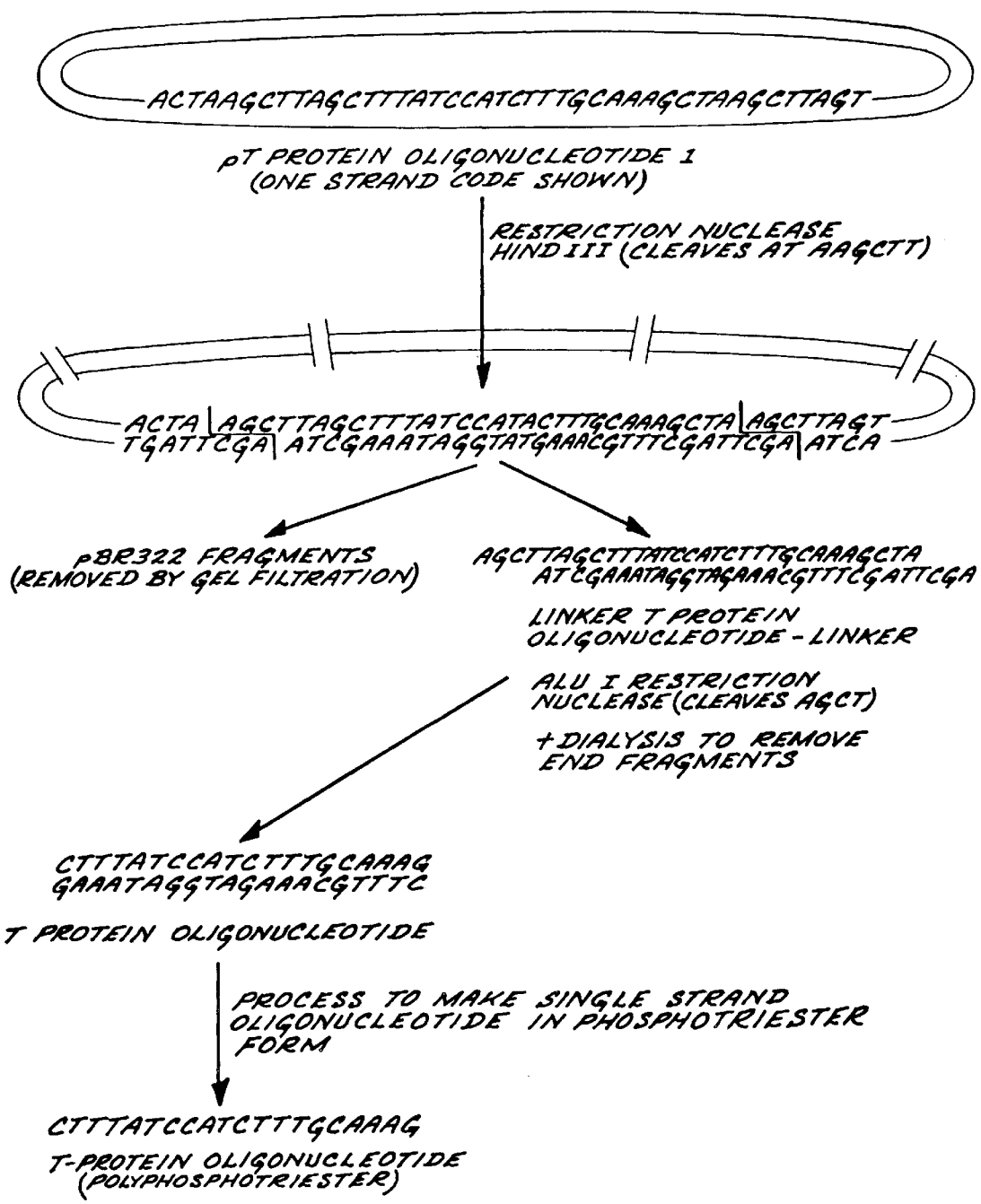

OLIGONUCLEOTIDE THERAPEUTIC AGENT AND METHODS OF MAKING SAME

This is a continuation of application Ser. No. 08/078,768, filed Jun. 16, 1993, which is a continuation of application Ser. No. 07/633,452, filed Dec. 20, 1990 (abandoned), which is a continuation of application Ser. No. 07/355,140, filed May 15, 1989 (now U.S. Pat. No. 5,023,243), which is a continuation of application Ser. No. 07/140,916, filed Dec. 29, 1987, now abandoned which is a continuation of application Ser. No. 07/002,014, filed Jan. 9, 1987, now abandoned which is a continuation of application Ser. No. 06/314,214, filed Oct. 23, 1981 now abandoned.

BACKGROUND OF THE INVENTION

This invention relates generally to controlling biologic functions, such as for antibiotic purposes, and more particularly, to utilizing hybridization techniques of the type having messenger ribonucleic acid attached to oligonucleotides for in vivo protein synthesis regulation.

In the field of pharmacology, the use of therapeutic agents has long been recognized as an effective way to control diseases. Such agents are often used in treating bacterial or viral infections, chemical imbalances and the like, to cure, or at least mitigate, the diseased state. Although researchers occasionally discover new therapeutic agents after major break-throughs have elucidated the molecular basis of a disease, more often they must rely on observing for antibiosis or modifying the chemical structures of functionally related chemicals.

With respect to antibiotic agents, some are quite effective at the outset, but over time many organisms become resistant or totally immune to their action. Additionally, very few effective anti-viral agents have ever been developed, and without explicit, detailed knowledge of an infecting organism's physiology, the development of new operative agents remains haphazard.

Thus, there exists a definite need for a methodology enabling the systematic design of new antibiotics and other therapeutic agents that is versatile and inexpensive, yet produces agents that are both extremely specific and effective. The present invention fulfills these needs.

SUMMARY OF THE INVENTION

The present invention provides a methodology of identifying and constructing therapeutic and other agents for use in living organisms that substantially reduces the uncertainty surrounding the development of new antagonists, significantly increasing the scope of materia medica. Moreover, the agent construction of the present invention lends itself readily to simple manufacture, even in large quantities, is extremely effective in use, and attains its improved results without undue cross-reactions.

In a presently preferred embodiment of the invention, by way of example and not necessarily by way of limitation, a stabilized oligonucleotide, preferably in a phosphotriester form, is provided having a base sequence substantially complementary to a portion of messenger ribonucleic acid coding for a biological component of an organism. Due to the complementary nature of the oligonucleotide and the messenger ribonucleic acid, the two components can readily hybridize under appropriate conditions to control synthesis of the organism's biological component and, if the protein is vital to the organism s viability, to act as an antibiotic.

A method, in accordance with the present invention, of developing therapeutic agents may typically include the steps of: providing a base sequence of an organism's nucleic acid that contains at least a portion of the genetic information for a biological component of the organism, and synthesizing an oligonucleotide the sequence of which is derived from the base sequence, for subsequent hybridization with the messenger ribonucleic acid specific for the biological component. The biological component may be a vital protein, or simply a hormone such as the gonadotropin, follicle stimulating hormone. The order of the base sequence may be determined from deoxyribonucleic acid (DNA) or ribonucleic acid (RNA), preferably messenger ribonucleic acid (mRNA). Alternatively, the desired oligonucleotide base sequence may be determined from the biological component's sequence, as when the biological component is a protein. The preferred oligonucleotide has a minimum of about fourteen or more bases, such as about twenty-three bases, and for increased stability, may be transformed to a more stable form, such as a phosphotriester form, to inhibit degradation during use.

To produce large quantities of the oligonucleotide, it may be synthesized chemically, such as in automated machines, or inserted into a plasmid, such as pBR322, for cloning. The plasmid insertion may be accomplished with linker base sequences, such as GATTCGAATC or CTAAGCTTAG, which are susceptible to degradation by Hind III restrictive nuclease or Alu I restriction nuclease. When the order of the base sequence has not been determined, the base sequence can be cloned and then cross-hybridized against messenger ribonucleic acid from the other sources to remove base sequences non-specific to the target.

Another aspect of the present invention is a method of selectively controlling activity of one or more biological components in a cell without substantially interfering with the activity of other biological components in the cell. The method includes the steps of forming an oligonucleotide having a base sequence substantially complementary to a portion of mRNA coding for the specific biological component, and introducing the oligonucleotide into the cell for hybridization with the selected mRNA. This causes blocking of the translation of the mRNA into protein. The oligonucleotide may have at least about fourteen bases or more, such as about twenty-three bases. The target mRNA can code for a protein, such as the hormone, follicle stimulating hormone. This hormone has an alpha and beta chain, and the oligonucleotide should be specific for the mRNA coding for the beta chain to avoid cross-reacting with other gonadatropin mRNA. A suitable oligonucleotide base sequence would be ACCACGCGR$_1$CCR$_2$ATGACGATGTG, wherein R$_1$ is G or T and R$_2$ is also G or T.

In accordance with another aspect of the present invention, a method is provided for inhibiting the infection of a host organism by a foreign organism. This method entails isolating a base sequence containing at least a portion of the genetic information coding for a vital protein from the foreign organism's nucleic acid; synthesizing an oligonucleotide, the order of which is derived from the base sequence and substantially complementary to the messenger ribonucleic acid coding for the protein; and treating the foreign organism with an effective amount of the oligonucleotide to hybridize with a portion of the messenger ribonucleic acid and block translation of the protein. The oligonucleotide, which can be a deoxyribonucleotide, can be transformed to a more stable form, such as a phosphotriester form, to inhibit degradation, and the order of the sequence determined prior to its synthesis. Further, to increase the oligonucleotide's specificity, it may be cross-hybridized against mRNA from different organisms, such as the host organism, to remove non-unique oligonucleotide sequences.

It will be appreciated from the foregoing that the present invention satisfies a long existing need for improved methods of developing therapeutic agents for use in living organisms, and represents a significant advance over previously available methods, principally because it is very versatile, and yet provides a very specific agent against a biological component. Other aspects and advantages of the invention will become apparent from the following more detailed description taken in conjunction with the accompanying drawings.

BRIEF DESCRIPTION OF THE DRAWINGS

FIG. 1 is a flow diagram showing the central dogma of molecular biology;

FIG. 2 is a flow diagram showing normal translation of messenger ribonucleic acid (mRNA) into T protein, as well as a synthetic oligonucleotide of the present invention blocking translation of the T protein;

FIG. 3 is a list of the viral deoxyribonucleic acid (DNA) code specific for SV-40 T protein, and the related mRNA and oligonucleotide;

FIG. 4 is a flow diagram showing the construction of high yield plasmids containing the T protein oligonucleotide;

FIG. 5 is a flow diagram showing the use of restriction nucleases to cleave the plasmids to give a purified T protein oligonucleotide;

FIG. 7 is a chart showing the partial amino acid sequence of follicle stimulating hormone, as well as the predicted mRNA sequence and related oligonucleotide family.

DETAILED DESCRIPTION OF THE INVENTION

Figure 6:
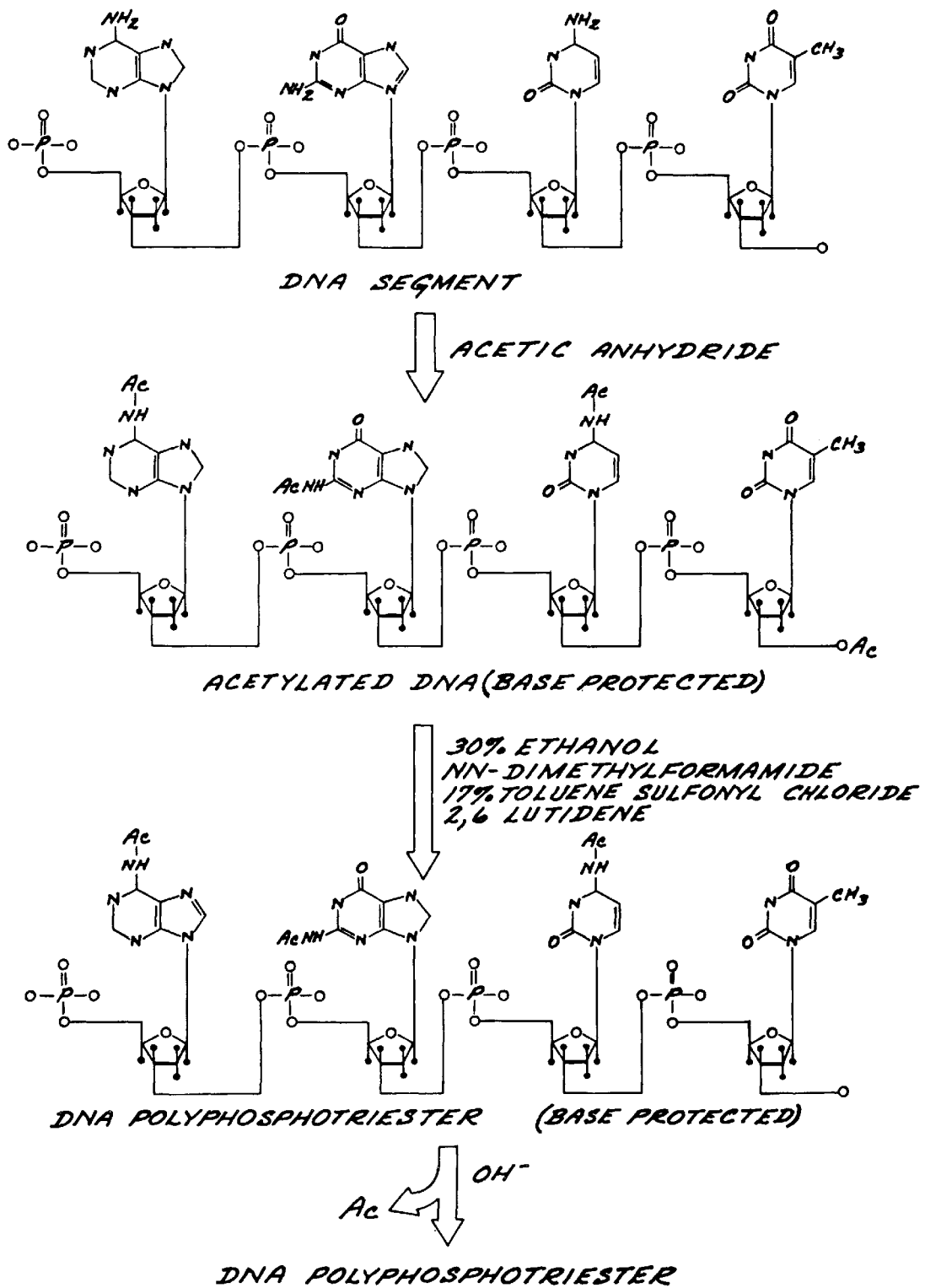
FIG. 6 is a flow diagram showing the treatment of a DNA sequence to form DNA polyphosphotriesters.

Referring now to the drawings, and particularly to FIGS. 1 and 2, there is shown the so-called "central dogma" of the molecular biology of life. Basically, it is now accepted that deoxyribonucleic acid (DNA) carries the genetic code for almost all living organisms. The code exists in the form of an organized sequence of four nucleotide bases attached to a phosphorylated, deoxyribose'sugar backbone. Generally, DNA exists in the form of a double strand helix formed of two oppositely directed strands, which are held together in an opposing manner by various weak forces.

A primary constituent of these weak forces are the so-called hydrogen bonds that exist between nucleotides on the opposing strands. The four bases, adenine (A), cytosine (C), guanine (G), and thymine (T), form hydrogen bonds generally only one fashion: A with T and C with G. Thus, by knowing the sequence of one strand, the sequence of the second strand can be readily determined.

Another aspect of the central dogma is that proteins are produced indirectly from the DNA strand, through messenger ribonucleic acid (mRNA). Apparently, mRNA, which has the same structure as single stranded DNA except with a ribose backbone and with uracil (U) replacing thymine, is transcribed directly from one DNA strand and has an essentially opposite base sequence, i.e., if a DNA strand sequence is 5'. . . ACGT . . . 3' the transcribed mRNA sequence is 3'. . . UGCA . . . 5'.

An additional aspect of the central dogma relates to the translation of mRNA into proteins. Briefly, excluding initiation sites and the like, each three nucleotide base grouping (triplet code) codes for one amino acid of a protein. Therefore, by knowing the mRNA sequence of a protein, its amino acid sequence can generally be determined. However, the reverse is not true, that is, knowing the amino acid sequence does not guarantee precise knowledge of the mRNA sequence. This stems from the fact that there exist 64 ($4^3$) possible triplet codes, yet there exists only about twenty amino acids, allowing some amino acids to have multiple triplet codes.

The similarity in the structure of DNA and mRNA strands creates interesting effects. Most notably, if complementary DNA and RNA strands exist contemporaneously in a solution, under certain established conditions the strands can anneal, forming hybrids. One important factor in proper annealing is the melting temperature, which can be calculated according to Britten et al, Methods of Enzymology 29:363 (1974).

In accordance with the present invention, a synthetic oligonucleotide having a base sequence capable of substantially matching that of a chosen mRNA is provided for hybridization with that mRNA. Once such a hybrid exists, the translation of the mRNA into protein becomes significantly inhibited. If the inhibited protein is vital to an organism's survival, the organism's viability, i.e., either growth or continued life, is jeopardized. Importantly, the oligonucleotide can be designed specifically for the mRNA coding for just one protein, and should not cross-react with mRNA for other proteins.

The method of developing the oligonucleotide entails basically two steps. As described more fully below, a possible first step is to determine the appropriate sequence of the mRNA specific for the protein to be inhibited, and a second step is to manufacture an oligonucleotide complementary to the mRNA. Once made, the oligonucleotide can be treated into a phospho-<triester form for increased stability.

A variety of techniques exists for determining nucleic acid base sequences. In many instances the sequence of the mRNA or the gene have been determined and published in the biochemical literature. In fact, researchers have determined the complete nucleotide sequence for the SV-40 virus (Reddy et al, Science 200:494 (1978)). As is well known, an alternative method entails isolating and purifying mRNA in sufficient quantities to permit sequencing studies, but this can prove difficult due to the relative instability and, in some cases, extreme rarity of many mRNA sequences.

Still another method for determining nucleic acid base sequences requires resolving the amino acid sequence from the target protein. After determining the amino acid sequence of the target protein in purified form, a sequential degradation utilizing commercially available protein sequencors (e.g. from Beckman Instruments, Fullerton, Calif.) can be used to provide the amino acid sequence. Once this has been obtained, knowledge of the triplet code can be applied to give prospective base sequences. An example of such a process for the hormone glucagon can be found in Tullis et al, Biochemical and Biophysical Research Communications 93:941 (1980).

Once the sequence of the appropriate nucleic acid and the desired mRNA sequence have been determined, an oligonucleotide, such as a deoxyribonucleotide, complementary to the mRNA can be constructed. A number of synthetic techniques are known, most typical is the diester approach described by Agarwal et al, Nature 227: 27 (1970), and oligonucleotide synthesizers may be purchased commercially from Vega Biochemicals, P.O. Box 11648, Tucson, Ariz. and Biologicals, Inc., Toronto, Canada.

If the desired oligonucleotide sequence is unknown, a suitable oligonucleotide can be prepared as follows. After isolating mRNA from a target organism, multiple copies are made, preferably in the form of DNA, so-called copy DNA (cDNA). This cDNA is then cross-hybridized against mRNA isolated from other organisms, and any cDNA hybridizing is removed. The remaining cDNA is specific only to the target organism, and can serve as the therapeutic agent.

In order to obtain a high degree of specificity, an oligomer of about fourteen or more residues can be constructed. Although shorter sequences will work, longer sequences provide higher specificity. This can readily be seen mathematically. Whereas a ten unit polymer chosen from four bases can have $4^{10}$ (1,048,576) ramdom combinations, a 20-unit polymer has $4^{20}$ random combinations, which equals $1.09 \times 10^{12}$ (1,090,000,000,000).

In spite of the added difficulty in making oligonucleotides of twenty units in comparison to ten bases, it is warranted because the exponential increase in complexity reduces undesirable cross-reactivity. It has been estimated that a mammalian cell contains about $2 \times 10^8$ nucleotides of RNA complexity or, in other words, approximately 200 million nucleotides of unique sequence mRNA, which is equivalent to about 30,000 mRNA sequences. The probability that one of those sequences contains a randomly chosen 20-unit polymer is approximately one in fifty-five hundred. In comparison, a ten-unit polymer has about a one hundred and ninety to one chance for random cross-reaction.

The present invention is illustrated by, but not limited to, the following examples.

EXAMPLE 1

SV-40 virus manufactures a vital protein commonly known as the "T protein" or "T antigen protein". As noted earlier, the complete genetic code for the SV-40 virus has been determined, and it is known that residues 5091 to 5071 on the viral genome code for a portion of the T protein mRNA. The sequence of these residues, the viral T protein mRNA sequence, and the designed T protein specific oligonucleotide are shown in FIG. 3. In this case, the T protein specific oligonucleotide is complementary to the viral T protein mRNA, and identical to the portion of the viral DNA code.

Prior to testing the effectiveness of the T protein specific oligonucleotide in vivo, the oligonucleotide can be mixed with total mRNA from an organism to check for cross-reactivity. If it hybridizes, then a different portion of the viral genome coding for the T protein should be utilized. Otherwise, the oligonucleotide is ready for further testing.

Further testing requires growth of S-40 virus. For purposes of these experiments, SV-40 virus is grown and titered in African green monkey cells, such as the cell line BSC-1, according to Hopps et al, Journal of Immunology 91:416 (1963). The identity of the virus can be confirmed by the following methods:

a) checking for tumor production after innoculation of the newborn hamsters with the virus;

b) neutralization of the virus by anti-SV-40 anti-serum; and c) reaction of the infected cells with anti-SV-40 T antigen directed antibodies prepared by standard techniques.

The isolation of SV-40 mRNA can be accomplished as follows. Total RNA is first obtained by the guanidine hydrochloric acid extraction procedure using glassware previously baked and treated with diethylpyrocarbonate to remove traces of RNase as taught by Cox et al, Methods in Enzymology 12B:120 (1968). The A+ RNA is isolated on oligo-dTcellulose, which can be obtained from Collaborative Research, Waltham, Mass., or P. L. Biochemicals, Inc., Milwaukee, Wis., utilizing the technique described by Bantle et al, Analytical Biochemistry 72:413 (1976). The RNA fractions are assayed for purity and intactness by electrophoresis according to the method described in Bailey et al, Analytical Biochemistry 70:75 (1976). Also, the RNA can be assayed for translatability in the wheat embryo in vitro system described in Marcus, et al, Methods in Enzymology: 30:749 (1974). The in vitro translation products are monitored on sodium lauryl sulphate 9% polyacrylamide gels as described in Laemmeli, Nature 227:680 (1970).

This purified A+ mRNA containing the viral mRNA sequences can hybridize to the synthetic oligonucleotide at 37° C. in 0.5M sodium phosphate buffer, pH 6.8, containing 0.2% sodium lauryl sulphate. Solutions containing about 1 mg A+ mRNA and synthetic oligonucleotide at a concentration of about 100 ug/ml are heated to 100° C. for 1–2 minutes, then cooled to 37° C. and allowed to anneal. The extent of the hybridization reaction as a function of time may be monitored on a gel filtration column.

Actually, while any theoretically suitable temperature may be used for the hybrid formation, temperatures ranging from 0° C. to about 80° C. provide for good hybridization, but preferred temperatures range from about 10° C. to about 40° C. Generally, the optimal annealing temperature for the formation of specific hybrids is believed to be about 20° C. to 25° C. below their melting temperature. Synthetic oligonucleotides operating at 37.5° C. should thus be designed on the basis of their base sequence and length, such that the melting temperature is between about 57° C. an 62° C. when tested under approximately physiological conditions.

For hybridization testing the ratio of the synthetic oligonucleotide to its mRNA complement is generally about 30:1. Lower ratios are acceptable, however, sequences below about 3:1 can cause lower hybrid formation. Control reactions utilizing yeast RNA or globin mRNA can be used, and should show no detectable hybrids, indicating hybridization specificity only to SV-40 mRNA. Also, thermal denaturation profile studies and comparison of the kinetics of hybridization can confirm that the synthetic oligonucleotide reacts only with SV-40 mRNA sequences.

Once it is shown that the oligonucleotide hybridizes to the isolated SV-40 mRNA, in vitro translation tests can be attempted utilizing the wheat embryo system (described previously) to show that the hybrid is not translated. Basically, upon introduction of SV-40 mRNA into the wheat embryo system, the system produces large T antigen protein. However, when an equal amount or more of synthetic oligonucleotide is also added to the system, T antigen protein synthesis can be substantially inhibited, without interference with synthesis of other SV-40 proteins whose mRNA was also introduced.

Testing of the oligonucleotide in vivo can be accomplished by adding the oligonucleotide to cultures of cells infected with SV-40. Synthesis of T antigen protein should be inhibited significantly in about six hours, and SV-40 growth should be strongly inhibited within about 24 hours. The growth of control cultures should be largely unaffected.

The synthetic oligonucleotide of the present invention may be mass produced according to common cloning techniques, such as those developed in the art to clone the gene for proinsulin. Alternatively, the oligonucleotide can be chemically synthesized in commercially available equipment (described previously). Briefly, the cloning method entails enzymatic insertion of the oligonucleotide into a bacterial gene carried on a larger piece of DNA, known as a plasmid. The plasmid can be incorporated into a suitable host bacteria, and multiple copies made as the bacteria multiply as in Boyer and Cohen, U.S. Pat. No. 4,237,224.

More particularly, and with reference to FIGS. 4 and 5, the cloning plasmid designated as pBR322, available from Bethesda Research Labs, Inc., Rockville, Md., can be used to mass produce the T protein specific oligonucleotide. Using standard techniques, the oligonucleotide is converted to double stranded form and then a terminal 5'$PO_4$ is added to each of the 5' termini with polynucleotide kinase to permit subsequent joining through T-4 ligase. The reaction conditions for forming the 5' termini can be found in Richardson, Progress in Nucleic Acids Research 2:815 (1972).

After purification of the double stranded oligonucleotide by chromatography on hydroxylapatite columns, it is inserted into the plasmid. Because the oligonucleotide is blunt ended, the plasmid should not have uneven or "sticky" ends. To remove sticky ends from the plasmid, S1 nuclease or other single strand specific nucleases can be utilized. A general description of methods for using restriction nucleases can be found in Nathans and Smith, Annual Review of Biochemistry 44: 273 (1975).

For best results, a linker system between the oligonucleotide and the plasmid can be utilized, specifically a linker having both Hind III and Alu I enzymatic cleaving sites. As seen in FIG. 4, one such linker has a sequence: 5'. . . CTAAGCTTAG . . . 3'. This sequence represents a double stranded, bisymmetric molecule containing a recognition sequence both for Alu I (AGCT) and for Hind III (AAGCTT). Utilizing DNA ligase under standard conditions, this molecule can be ligated to the oligonucleotide to form linker-oligonucleotide-linker molecules. Similarly, the linked oligonucleotide can be introduced into linearized bluntended, Hind III cleaved pBR322 carrier molecules.

After ligation, the plasmid has resumed its covalently closed circular configuration with the linker-oligonucleotide incorporated, all of which is shown in FIG. 5 as pT-protein oligonucleotide. The recircularized plasmid is then used to transform a suitable bacterial host such as *E. coli*. The methods for transformation and selection of transformants are known in the art and described in detail in Cohen and Boyer, U.S. Pat. No. 4,237,224.

Once the transformed bacteria containing the ligated plasmid p-oligonucleotide have been grown to high density and produced large amounts of the ligated plasmid, the oligonucleotide is ready for purification. After the plasmid has been removed from the mature cells, the plasmid is treated with appropriate restriction endonucleases. As illustrated in FIG. 5, the plasmid is first cleaved with Hind III to give various by-products, including linker-T-protein-oligonucleotide-linker and fragments of the original plasmid. These are readily separated utilizing gel electrophoresis or high pressure liquid chromatography. Further cleavage of the isolated linker-oligonucleotide-linker with the endonuclease Alu I yields pure double stranded oligonucleotide and partially degraded linker. These can also be separated based on their size differences.

As shown in FIG. 6, the oligonucleotide can then be modified to a nuclease resistant phosphotriester form utilizing the reaction described in Miller et al, Biochemistry 16:1988 (1977). Basically, the oligonucleotide is first acylated using 50% acetic anhydride-pyridine during an overnight incubation period. The product is precipitated and isolated from ether. The phosphotriester can then be formed utilizing 30% ethanol in anydrous 2, 6 lutidene (30%), NN-dimethyl formamide (30%) and p-toluene sulfonyl chloride (17%), and reacting for about 6 hours. The protecting acetyl groups are then hydrolyzed by the addition of 0.5 volumes of concentrated ammonium hydroxide, followed by incubation for about 1 hour at 55° C. The final oligonucleotide product in the ethyl phosphotriester form can then be isolated on paper chromatography or high pressure liquid chromatography.

It is believed that transforming the oligonucleotide to a phosphotriester form will improve the oligonucleotide's stability in vivo due to an enhanced resistance against various degradative enzymes. However, the oligonucleotide will eventually degrade because of spontaneous de-ethylation, which leaves the molecule unprotected. Indeed, by controlling the initial level of ethylation, the in vivo degradation rate can be controlled. A further advantage of a phosphotriester form is believed to be an increase in the oligonucleotide's ability to penetrate a cell membrane.

EXAMPLE 2

A synthetic oligonucleotide capable of inhibiting the synthesis of follicle stimulating hormone (FSH), a protein hormone produced by the pituitary that functions in the maturation of ova in females and sperm cells in males, can also be constructed. It is known that FSH is composed of two chains, alpha and beta, the amino acid sequence of which has been determined for several animal species. Interestingly, the alpha chain of FSH is common to other gonadotropic hormones, including thyroid stimulating hormone, luteinizing hormone, and chorionic gonadotropin, while the beta chain varies. Therefore, to selectively shut off the synthesis of FSH without substantially affecting the other gonadotropins, the oligonucleotide must be specific for the mRNA coding for the beta chain.

The sequence of the beta chain amino acids 32 through 40 is shown in FIG. 7. As discussed earlier, it is possible to predict the mRNA base sequence for these amino acids, although not with absolute certainty. The points of uncertainty are indicated by the letter "X" in the predicted mRNA sequence. Thus, the resultant oligonucleotide family consists of eight possible 26 base sequences; the potential alternate bases are shown in parentheses below the primary base sequence.

By beginning with the projected mRNA sequence for the 33rd through 40th amino acids, it can be seen that four different 23 base oligonucleotides exist that could correspond to the FSH mRNA. The sequences could be as follows, reading from the 5' end: GTGTAGCAGTAGCCGGCGCACCA, GTGTAGCAGTATCCGGCGCACCA, GTGTAGCAGTAGCCTGCGCACCA, and GTGTAGCAGTATCCTGCGCACCA.

One of these four sequences should be precisely correct and thus able to hybridize fully with the FSH mRNA. To determine the best sequence, a hybridization test against FSH mRNA, with subsequent purification on hydroxylapatite or other suitable column, can be performed as previously described. Once the best sequence has been determined, it is placed in a plasmid or chemically synthesized, as described above, for bulk synthesis. This oligonucleotide should substantially inhibit the synthesis of FSH in vivo.

From the foregoing, it will be appreciated that the present invention provides a systematic method of designing new therapeutic agents for use in living organisms and that this method is versatile and inexpensive. Further, the oligonucleotide produced in accordance with the present invention is extremely effective and specific, enabling selective control of protein synthesis in a living organism.

While several particular forms of the invention have been illustrated and described, it will be apparent that various modifications can be made without departing from the spirit and scope of the invention. Accordingly, it is not intended that the invention be limited, except as by the appended claims.

I claim:

1. A method of selectively inhibiting the expression of a target protein in a cell producing messenger ribonucleic acids encoding the target protein and other proteins without inhibiting the expression of the other proteins, with the proviso that the cell is in a cell culture, said method comprising the steps of:

(i) synthesizing an oligonucleotide having a base sequence substantially complementary to a subsequence of a messenger ribonucleic acid said subsequence coding for the target protein said oligonucleotide stabilized to inhibit degradation by nucleases;

(ii) introducing the oligonucleotide into the cell; and (iii) hybridizing the oligonucleotide to the subsequence of the messenger ribonucleic acid to inhibit the expression of the target protein.

2. A method of claim 1 wherein the entire sequence of the oligonucleotide is complementary to the subsequence of a messenger ribonucleic acid coding for the target protein.

3. A method of claim 1 wherein the oligonucleotide is at least 14 bases in length.

4. A method of claim 1 wherein the oligonucleotide is about 23 bases in length.

5. A method of claim 1 wherein the oligonucleotide is between 14 and 23 bases in length.

6. A method of claim 1 wherein the messenger ribonucleic acid is viral.

7. A method of claim 1 wherein the messenger ribonucleic acid encodes a hormone.

8. A method of claim 1 wherein the oligonucleotide is a oligodeoxynucleotide.

9. A method of selectively inhibiting the expression of a target protein in a cell producing messenger ribonucleic acids encoding the target protein and other proteins without inhibiting the expression of the other proteins with the proviso that the cell is in a cell culture, said method comprising the method of:

(i) synthesizing an oligonucleotide having a base sequence substantially complementary to a subsequence of a messenger ribonucleic acid said subsequence coding for the target protein;

(ii) introducing the oligonucleotide into the cell; and (iii) hybridizing the oligonucleotide to the subsequence of the messenger ribonucleic acid to inhibit the expression of the target protein.

10. A method of manufacturing an oligonucleotide having a base sequence able to inhibit expression of a protein encoded by an mRNA inside a cell with the proviso that the cell is in a cell culture, said method comprising the steps of:

(i) synthesizing an oligonucleotide having a base sequence complementary to the coding region of the mRNA encoding the protein; and (ii) contacting the cell with an amount of oligonucleotide effective to inhibit the expression of the protein.

11. A method of claim 10 wherein the synthesis is a chemical synthesis.

12. A method of claim 10 wherein the oligonucleotide is between 14 and 23 bases in size.

13. A method of claim 10 wherein the oligonucleotide is stabilized to be resistant to degradation.

* * * * *